(12) United States Patent
Welti et al.

(10) Patent No.: US 8,095,522 B2
(45) Date of Patent: Jan. 10, 2012

(54) METHOD OF SEARCHING FOR INFORMATION IN A DATABASE

(75) Inventors: Paul Welti, Paris (FR); Jean-Christophe Fondeur, Alexandria, VA (US)

(73) Assignee: Morpho, Paris (FR)

( * ) Notice: Subject to any disclaimer, the term of this patent is extended or adjusted under 35 U.S.C. 154(b) by 558 days.

(21) Appl. No.: 11/792,866

(22) PCT Filed: Dec. 13, 2005

(86) PCT No.: PCT/FR2005/003112
§ 371 (c)(1),
(2), (4) Date: Jun. 12, 2007

(87) PCT Pub. No.: WO2006/064119

PCT Pub. Date: Jun. 22, 2006

(65) Prior Publication Data

US 2007/0299876 A1    Dec. 27, 2007

(30) Foreign Application Priority Data

Dec. 13, 2004   (FR) ..................................... 04 13210

(51) Int. Cl.
*G06F 7/00*   (2006.01)
(52) U.S. Cl. ...................................................... 707/705
(58) Field of Classification Search ............. 707/104.1, 707/999.107, 705, 941; 600/26, 27
See application file for complete search history.

(56) References Cited

U.S. PATENT DOCUMENTS

| | | | |
|---|---|---|---|
| 5,596,994 A * | 1/1997 | Bro | 600/545 |
| 6,102,846 A * | 8/2000 | Patton et al. | 600/26 |
| 2003/0108241 A1 | 6/2003 | Colmenarez et al. | |
| 2003/0165270 A1* | 9/2003 | Endrikhovski et al. | 382/189 |
| 2004/0024287 A1* | 2/2004 | Patton et al. | 600/27 |
| 2004/0176991 A1* | 9/2004 | McKennan et al. | 705/10 |

FOREIGN PATENT DOCUMENTS

WO   WO-94/08311 A1   4/1994

OTHER PUBLICATIONS

Bruno Verschuere, Geert Crombez, Armand De Ciercq, Ernst H. W. Koster, Autonomic and behavioral respnding to concealed information: differentiating orienting and defense reponses, May 2004, Phsychophysiology, vol. 41, issue 3, pp. 461-466.*
Picard et al., "Modeling User Subjectivity in Image Libraries," MIT Media Laboratory, IEEE, 1996, pp. 777-780.
Wu et al., "Identifying Faces Using Multiple Retrievals," National University of Singapore, IEEE Media, 1994, pp. 27-38.

* cited by examiner

*Primary Examiner* — Angela Lie
(74) *Attorney, Agent, or Firm* — Muncy, Geissler, Olds & Lowe, PLLC

(57) ABSTRACT

The present invention relates to a method of searching for information in a database, the method comprising the steps of:
  presenting at least one item of data to an observer and measuring at least physiological parameter of the observer; and
  in the presence of a variation in the physiological parameter greater than a predetermined threshold, presenting an item of data having a relationship with the previously-presented data item.

9 Claims, 1 Drawing Sheet

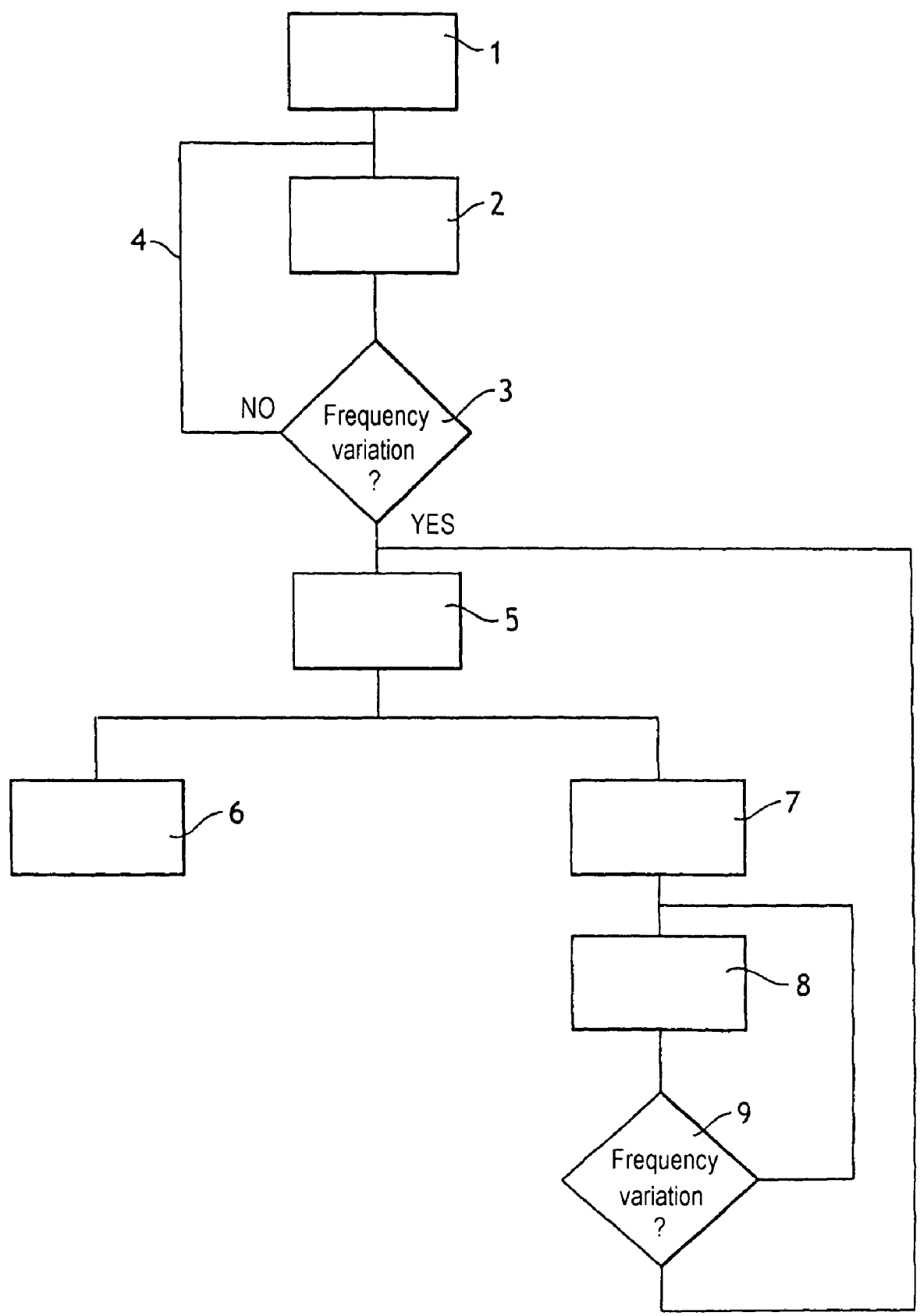

METHOD OF SEARCHING FOR INFORMATION IN A DATABASE

The present invention relates to a method of searching for information in a database.

BACKGROUND OF THE INVENTION

After an assault, detectives generally attempt to identify the attacker by showing the victim or witnesses portraits of individuals contained in a police database in order to enable the victim or the witnesses to recognize the attacker therein. Another method of identification consists in reconstituting the face of the attacker by making a composite (Identikit) portrait with the help of the victim or the witnesses. Unfortunately, it can happen that the victim or the witnesses repress, forget, are too frightened to say, or did not consciously see the face of the attacker, thus making an identification of the attacker by those methods impossible. In addition, consulting databases of portraits or making a composite portrait are operations that are relatively lengthy and require sustained attention on the part of the victim, who is generally upset or in a state of shock, or indeed injured. These operations are thus particularly arduous for the victim and also for the witnesses who may likewise be suffering emotionally.

Document WO-A-94/08311 thus describes a method of searching a database of portraits for police purposes, in which portraits are selected as a function of a characteristic that the witness judges to be important.

Document US-A-2003/108241 discloses a method of consulting a database that has previously been sorted as a function of a connection between the data and the emotional state of a habitual user, the consultation comprising, at the beginning of a consultation of the database, a step of detecting at least one physiological parameter of the user that is representative of the user's emotional state, so as subsequently to present to the user data that corresponds to said emotional state. Implementing that method assumes that the data has previously been given a parameter that is representative of emotional state as a function of the user, since the search is performed on the basis of that parameter. This is not applicable to searching through a database when the user is confronted with that database for the first time. Furthermore, that method is not usable if numerous users are likely to make use of that database.

In a similar approach, document US-A-2003/165270 proposes marking images presented to an observer as a function of the reaction of the observer viewing those images.

The document "Identifying faces using multiple retrievals" (Kian Kang Wu et al., IEEE Multimedia, IEEE Computer Society, US, Vol. 1, No. 2, Jun. 21, 1994) discloses a method of searching a database by using parameters that are weighted as a function of their importance, and the document "Modeling using subjectivity in image libraries" (Picard, Minutes de la Conférence Internationale de Traitement de l'image ICIP [Minutes of the International Conference on Image Processing], Lausanne, IEEE, US, Vol. 16, Sep. 16, 1996) describes a method of evaluating the similarity of two images.

OBJECT OF THE INVENTION

It would therefore be advantageous to have means serving to facilitate and optimize searching for information in a database, in particular in order to hasten recognition of an individual.

BRIEF SUMMARY OF THE INVENTION

To this end, the invention provides a method of searching for information in a database, the method comprising the steps of:

presenting at least one item of data to an observer and measuring at least physiological parameter of the observer; and in the presence of a variation in the physiological parameter greater than a predetermined threshold, presenting an item of data having a relationship with the previously-presented data item.

The physiological characteristic to which the data relates may be the morphology, the face, the voice, . . . , and observing it may require one or more of the observer's senses to be involved. The measured physiological parameter may be heart rhythm, a parameter associated with blood flow such as the blood being saturated in oxygen, or vasodilation, saliva flow, a muscular reaction such as a sudden contraction or trembling, sweating, . . . . Thus, variation in the physiological parameter of the observer constitutes a reaction of the observer to the presentation of the data, which reaction is unconscious or at least involuntary, and serves to identify relatively quickly which data is similar to the information being sought. The physiological parameter is not a field in the database that is used as a search parameter, but an index of the emotional impact of the data item on the observer, or of the observer's interest therein. Thereafter, a search is made for data bearing some relationship, and more particularly similarity, with the previously-presented data item (the data item being sought itself has a relationship with the initially-presented item, i.e. both data items have contents that present a relationship with each other: this is not a relationship between parameters associated with the data items in the database). Taking into consideration the clue constituted by the variation in the physiological parameter thus serves to accelerate the search for information. This method also makes it possible to limit the amount of questioning of the observer and does not give the observer the impression of being subjected to interrogation. This method also makes it possible to limit the amount of explanation that needs to be given to the observer concerning how the presentation operates.

Other characteristics and advantages of the invention appear on reading the following description of a particular, non-limiting implementation of the invention.

BRIEF DESCRIPTION OF THE DRAWING

Reference is made to the sole accompanying FIGURE which is constituted by a block diagram showing one implementation of the method in accordance with the invention.

DETAILED DESCRIPTION OF THE INVENTION

With reference to the FIGURE, the method of the invention is described herein with respect to an observer recognizing an individual on the basis of information or data contained in a database and relating to the same physiological characteristic for a plurality of different individuals. In this example the physiological characteristic is the face, and the data is thus made up of portraits of those individuals.

The database is hosted on a computer server including calculation means and associated with a display screen.

The method of the invention as described herein is based on taking a physiological parameter into consideration in order to navigate in the database. The physiological parameter in question in this example is the frequency of heart beats, relying on the principle that an acceleration in heart frequency can be the result of an increase in the emotional tension of the observer or of the observer becoming stressed by viewing one of the portraits. In order to be taken into consideration, this increase needs to be greater than a threshold representative of variation in heart frequency that is not associated with emotional stress, but for example with the effort needed to change posture. Any physiological parameter can be selected insofar as it reveals an emotion, a reaction, or a particular behavior associated with examining a data item (e.g. showing interest).

The method begins with a calibration step 1 during which heart frequency is measured on the observer at rest in order to determine a nominal heart frequency under the circumstances. This measurement is performed in conventional manner, e.g. by means of a pulse meter.

The method then continues by a step 2 of presenting portraits to the observer while simultaneously measuring the observer's heart frequency and the viewing direction of the observer, with this being done in a manner that is itself known, e.g. by means of a eye tracker.

By way of example, the portraits are displayed on the display screen in groups.

In the absence of any variation in heart frequency greater than the predetermined threshold, and if the observer does not make any particular remarks, the next group of portraits is displayed (step 3, 4).

In the presence of a variation in heart frequency greater than the predetermined threshold (step 3), the portrait being looked at at the time heart frequency varies is determined on the basis of the viewing direction of the observer (step 5). In addition, detecting the viewing direction of the observer can serve to identify within the portrait as determined in this way, some portion that is of particular interest to the observer, either by measuring and comparing the durations with which different portions of the portrait are examined, or because viewing this portion is followed immediately by the change in heart frequency.

When the groups of portraits are scrolled automatically, the length of time each group of portraits is displayed must be long enough to allow for the change in heart frequency to occur, where appropriate.

The method then continues with a step 6 of giving scores to the portrait, e.g. as a function of:
  a degree of attention by the observer for the portrait in question, and in particular the number of times the observer looks towards the portrait or the length of time the portrait is viewed; and
  a characteristic of the variation, and in particular its amplitude, such as the maximum heart frequency reached or the acceleration of the heart rhythm.

A search 7 is then undertaken, and portraits are presented 8 that present some relationship with the portrait that gave rise to a variation in the heart frequency of the observer. This relationship is a relationship of similarity between the portraits. This similarity relationship can apply in preponderant manner to the portion of interest, if there is one. For example, if the heart frequency of the observer increased while the observer was looking at a particular beard on the determined portrait, then the portraits that are subsequently presented will have similar beards. Naturally, the same applies to eyes, the hair, the nose, the mouth, a scar, . . . . Naturally, this assumes that the database is organized accordingly. The portraits for presentation may also be determined by a principal component analysis, in real time or in parallel, in order to find points in common between the portraits for presentation and the portraits that gave rise to the variation in the heart frequency of the observer. The similarity relationship may take account of various portions of a face in weighted manner in order to take account of the relative importance of said portions in one individual recognizing another.

In the presence of a new variation in heart frequency (step 9), preceding steps 5 to 8 are repeated.

Numerous similar portraits are presented so long as the observer has not formally identified the looked-for individual. When all of the similar portraits in the database have been presented, or after a determined length of time has elapsed without an individual being identified, a list of the most probable candidates is established as a function of the scores given. These candidates may be those whose portraits triggered variation in heart rhythm, or portraits that are similar.

In a variant, it is possible to interrupt the presentation when one of the portraits is given a score that is greater than a predetermined threshold.

Naturally, the invention is not limited to the implementation described, and variant implementations can be provided without going beyond the ambit of the invention as defined by the claims.

In particular, the search method is not limited to searching information concerning faces, but could also relate to silhouettes, images of places, or images of objects. In addition, the search method is not limited to searching for visual information, but could apply to other senses, and in particular to hearing for sound information.

Naturally, other physiological parameters can be used, in particular if variation therein can reveal stress: a parameter associated with blood flow such as the blood becoming saturated in oxygen, vasodilation, or blood pressure; the saliva flow rate; a muscular reaction such as a sudden contraction or trembling; sweating (skin resistance); response time to a question following the presentation of information; breathing rhythm; voice (tension or trembling, inflection); hairs standing up; pupil diameter; facial expression (eye movement or mimicry, possibly changing the expressions of the face, a blinking reflex); posture (a protective reflex may change the observer's posture, such as a stapedial reflex); brain activity (activation of a particular zone of the brain); . . . . A plurality of physiological parameters can be monitored simultaneously in order to take variations therein into account.

Detecting the observer's viewing direction is optional, in particular when images are presented to the observer one by one.

In a variant, a step can be provided for evaluating the reliability of the search by using at least one pre-established resemblance criterion for comparing different items of information given scores above a predetermined threshold.

The invention claimed is:

1. A method to facilitate and optimize performing a search for information in a database, the method comprising the steps of:
  presenting one item of data from a database at a time to an observer and measuring at least a physiological parameter of the observer;
  in the absence of any variation in the physiological parameter greater than a predetermined threshold, and if the observer does not make any particular remarks, presenting at least one other item of data to the observer and measuring the physiological parameter of the observer;
  in the presence of a variation in the physiological parameter greater than a predetermined threshold, detecting on an image at least one portion of interest to the observer and presenting an item of data having a relationship of similarity with the previously-presented data item, the relationship existing between the previously-presented image and the image presented after detecting a variation in the physiological parameter relating to said portion of interest; and repeating all previous steps until at least one item of data from the database, which contains said information, is identified.

2. A method according to claim 1, the method including a prior calibration step in which the physiological parameter is measured in order to determine a nominal level thereof.

3. A method according to claim 1, wherein the portion of interest is detected by measuring the length of time said portion is examined.

4. A method according to claim 1, wherein the portion of interest is detected by identifying a correlation between viewing said portion and the variation in the physiological parameter.

5. A method according to claim 1, wherein the images are presented in groups, and wherein the method includes a step of detecting the observer's viewing direction while the images are being presented.

6. A method according to claim 1, the method including a step of scoring the information that triggered the variation in the physiological parameter, during which the information is given a score that takes account of the degree of the observer's attention for the portrait and/or a characteristic of the variation in the physiological parameter.

7. A method according to claim 6, wherein the presentation of information is interrupted when the score is greater than a predetermined threshold.

8. A method according to claim 6, the method including a step of evaluating the reliability of the search by using at least one pre-established resemblance criterion to compare the items of information that have a score greater than a predetermined threshold.

9. The method according to claim 1, wherein the database is a police database of possible suspects.

\* \* \* \* \*